US005665590A

United States Patent [19]

Yang

[11] Patent Number: 5,665,590

[45] Date of Patent: Sep. 9, 1997

[54] METHOD FOR ISOLATING AND DIRECTLY CLONING GENES WHICH ENCODE CELL-SURFACE AND SECRETED PROTEINS

[75] Inventor: Zhi Yang, Menlo Park, Calif.

[73] Assignee: SyStemix, Inc., Palo Alto, Calif.

[21] Appl. No.: 282,951

[22] Filed: Jul. 29, 1994

[51] Int. Cl.$^6$ .............................. C12N 5/10; C12N 15/85

[52] U.S. Cl. ......................... 435/6; 435/320.1; 435/172.3

[58] Field of Search ................................ 435/69.1, 69.3, 435/172.1, 172.3, 320.1, 69.7, 69.8, 6, 7.1, 7.2, 240.2

[56] References Cited

U.S. PATENT DOCUMENTS 5,525,486 6/1996 Honjo et al. .......................... 435/69.1

5,536,637 7/1996 Jacobs ........................................ 435/6

FOREIGN PATENT DOCUMENTS 0607054 7/1994 European Pat. Off. .

OTHER PUBLICATIONS

Tashiro et al., "Signal sequence trap: A cloning strategy for secreted proteins and type 1 membrane proteins" *Science* (1993) 261:600–603.

Sambrook et al., eds., *Molecular Cloning. A Laboratory Manual* (1989) 2nd Ed., vols. 1–3, Cold Spring Harbor Laboratory Press, Cold Spring Harbor, New York. The title page and table of contents are included herewith.

Ausubel et al., eds., *Current Protocols in Molecular Biology* (1993) vol. 2, Current Protocols, New York. The title page and table of contents are included herewith.

Fujisawa et al., "A transcriptional enhancer sequence of HTLV–I is responsible for trans–activation mediated by p40$^x$ of HTLV–I" *EMBO J.* (1986) 5:713–718.

Ohtani et al., "Identification of two distinct elements in the long terminal repeat of HTLV–I responsible for maximum gene expression" *EMBO J.* (1987) 6:389–395.

Takebe et al., "SRα promoter: an efficient and versatile mammalian cDNA expression system composed of the simian virus 40 early promoter and the R–U5 segment of human T–cell leukemia virus type 1 long terminal repeat" *Mol. Cell. Biol.* (1988) 8:466–472.

Metzger et al., "The human oestrogen receptor functions in yeast" *Nature* (1988) 334:31–36.

Fiers et al., "Complete nucleotide sequence of SV40 DNA" *Nature* (1978) 273:113–120.

Gluzman et al., eds., *Enhancers and Eukaryotic Gene Expression* (1983) Cold Spring Harbor Laboratory Press, Cold Spring Harbor, New York. The title page and table of contents are included herewith.

Seed, "An LFA–3 cDNA encodes a phospholipid–linked membrane protein homologous to its receptor CD2" *Nature* (1987) 329:840–841.

Evan et al., "Isolation of monoclonal antibodies specific for human c–myc protooncogene product" *Mol. Cell. Biol.* (1985) 5:3610–3616.

Wilson et al., "The structure of an antigenic determinant in a protein" *Cell* (1984) 37:767–778.

Ferguson et al., "Cell–surface anchoring of proteins via glycosyl–phosphatidylinositol structures" *Ann. Rev. Biochem.* (1988) 57:285–320.

Beaucage et al., "Deoxynucleoside phosphoramidites—a new class of key intermediates for deoxypolynucleotide synthesis" *Tetra. Letts.* (1981) 22:1859–1862.

Matteucci et al., "Synthesis of deoxyoligonucleotides on a polymer support" *J. Am. Chem. Soc.* (1981) 103:3185–3191.

Hemperly et al., "Sequence of a cDNA clone encoding the polysialic acid–rich and cytoplasmic domains of the neural cell adhesion molecule N–CAM" *Proc. Natl. Acad. Sci. USA* (1986) 83:3037–3041.

Barthels et al., "Isolation and nucleotide sequence of mouse NCAM cDNA that codes for a $M_r$ 79 000 polypeptide without a membrane–spanning region" *EMBO J.* (1987) 6:907–914.

Barthels et al., "High degree of NCAM diversity generated by alternative RNA splicing in brain and muscle" *Eur. J. Neurosci.* (1992) 4:327–337.

Crossin et al., "Expression of adhesion molecules and the establishment of boundaries during embryonic and neural development" *Exp. Neurol.* (1990) 109:6–18.

Tosney et al., "The distribution of NCAM in the chick hindlimb during axon outgrowth and synaptogenesis" *Dev. Biol.* (1986) 114:437–452.

Thiery et al., "Adhesion among neural cells of the chick embryo: II. Purification and characterization of a cell adhesion molecule from neural retina" *J. Biol. Chem.* (1977) 252:6841–6845.

Key et al., "Olfactory neurons express a unique glycosylated form of the neural cell adhesion molecule (N–CAM)" *J. Cell. Biol.* (1990) 110:1729–1743.

Edelman, "Morphoregulatory molecules" *Biochem.* (1988) 27:3533–3543.

Kanehisa, "Use of statistical criteria for screening potential homologies in nucleic acid sequences" *Nucl. Acids Res.* (1984) 12:203–213.

Mullis et al., "Specific enzymatic amplification of DNA in vitro: the polymerase chain reaction" *Quant. Biol.* (1986) 51:263–273.

Hanahan, "Studies on transformation of *Escherichia coli* with plasmids" *J. Mol. Biol.* (1983) 166:557–580.

Matthews et al., "A receptor tyrosine kinase specific to hematopoietic stem and progenitor cell–enriched populations" *Cell* (1991 ) 65:1143–1152.

Baum et al., "Isolation of a candidate human hematopoietic stem–cell population" *Proc. Natl. Acad. Sci. USA* (1992) 89:2804–2808.

Rosnet et al., "Human FLT3/FLK2 gene: cDNA cloning and expression in hematopoietic cells" *Blood* (1993) 82:1110–1119.

(List continued on next page.)

*Primary Examiner*—David Guzo

*Attorney, Agent, or Firm*—Morrison & Foerster LLP

[57] ABSTRACT

Methods and DNA cloning vectors are provided for obtaining genes encoding secreted proteins and cell surface proteins.

43 Claims, 7 Drawing Sheets

OTHER PUBLICATIONS

Anderson et al., "Molecular cloning of mast cell growth factor, a hematopoietin that is active in both membrane bound and soluble forms" *Cell* (1990) 63:235–243.

Chirgwin et al., "Isolation of biologically active ribonucleic acid from sources enriched in ribonuclease" *Biochem.* (1979) 18:5294–5299.

Veres et al., "The molecular basis of the sparse fur mouse mutation" *Science* (1987) 237:415–417.

Gu et al., "Cell cycle regulation of CDK2 activity by phosphorylation of Thr160 and Tyr 15" *EMBO J.* (1992) 11:3995–4005.

Tsai et al., "Isolation of the human cdk2 gene that encodes the cyclin A– and adenovirus E1A–associated p33 kinase" *Nature* (1991) 353:174–177.

Kaufman, "Vectors used for expression in mammalian cells" *Meth. Enzymol.* (1990) 185:487–511.

Ferguson, "Cell–surface anchoring of proteins via glycosyl–phosphatidylinositol structures" *Ann. Rev. Biochem.* (1988) 57:285–320.

Sabatini et al, "Mechanisms for the incorporation of proteins in membranes and organelles" *J. Cell. Biol.* (1982) 92:1–22.

Wilson et al., "The structure of an antigenic determinant in a protein" *Cell* (1984) 37:767–778.

Hirt, "Selective extraction of polyoma DNA from infected mouse cell cultures" *J. Mol. Biol.* (1967) 26:365–369.

FIG. 2

```
                                    30                                      60
CCC TGC AGA TCG ATG AGC TCG CTA GCC AGC TGC CAG TGT GAT GGC TGA CTT CTA GAG AAT
Pro Cys Arg Ser Met Ser Ser Leu Ala Ser Cys Gln Cys Asp Gly End Leu Leu Glu Asn

                                    90                                     120
TCC AGC ACA CTG GGC GGC CGC GAG CAG AAA CTG ATC TCT GAA GAA GAC CTG AAC TAC CCA
Ser Ser Thr Leu Gly Gly Arg Glu Gln Lys Leu Ile Ser Glu Glu Asp Leu Asn Tyr Pro

                                   150                                     180
TAC GAC GTC CCA GAC TAC GCT TAC CCA TAC GAC GTC CCA GAC TAC GCT TAC CCA TAC GAC
Tyr Asp Val Pro Asp Tyr Ala Tyr Pro Tyr Asp Val Pro Asp Tyr Ala Tyr Pro Tyr Asp

                                   210                                     240
GTC CCA GAC TAC GCT CCA AAT AAA GGA AGT GGA ACC ACT TCA GGT ACT ACC CGT CTT CTA
Val Pro Asp Tyr Ala Pro Asn Lys Gly Ser Gly Thr Thr Ser Gly Thr Thr Arg Leu Leu

                                   270                                     300
TCT GGG CAC ACG TGT TTC ACG TTG ACA GGT TTG CTT GGG ACG CTA GTA ACC ATG GGC TTG
Ser Gly His Thr Cys Phe Thr Leu Thr Gly Leu Leu Gly Thr Leu Val Thr Met Gly Leu

CTG ACT TAG GTA CC
Leu Thr End Val
```

FIG. 3

```
        10         20         30         40         50         60         70         80
CCCTGCAGAT CGATGAGCTC GCTAGCCAGC TGCCAGTGTG ATGGCTGACT TCTAGAGAAT TCCAGCACAC TGGGCGGCCG
  P   SCT      SA     N     PAB    B                   X     E     B      B     NXHF F
  S   ALA      AL     H     VLB    S                   B     C     S      S     OMAN N
  T   UAQ      CU     E     UUV    T                   A     O     T      R     TAEU U
  1   3A11     11     1     211    1                   1    R1     1      1     1331 2

        90        100        110        120        130        140        150        160
CGAGCAGAAA CTGATCTCTG AAGAAGACCT GAACTACCCA TACGACGTCC CAGACTACGC TTACCCATAC GACGTCCCAG
    A        S      M   M                      A                             A
    L        A      B   B                      A                             A
    W        U      O   O                      T                             T
    1       3A      2   2                      2                             2

                                                                                5
       170        180        190        200        210        220        230        240
ACTACGCTTA CCCATACGAC GTCCCAGACT ACGCTCCAAA TAAAGGAAGT GGAACCACTT CAGGTACTAC CCGTCTTCTA
                  A                                    NX            R          M
                  A                                    LM            S          B
                  T                                    AN            A          O
                  2                                    41            1          2

       250        260        270        280        290        300        310
TCTGGGCACA CGTGTTTCAC GTTGACAGGT TTGCTTGGGA CGCTAGTAAC CATGGGCTTG CTGACTTAGG TACC
   B   APA            H                  H           N N              D   KR
   S   FMF            I                  G           C L              D   PS
   P   LLL            N                  A           O A              E   NA
   6   313            2                  1           1 3              1   11
```

FIG. 4

```
                                        30                                          60
CCC TGC AGA TCG ATG AGC TCG CTA GCC AGC TGC CAG TGT GAT GGC TGA CTT CTA GAG AAT

                                        90                                         120
TCC AGC ACA CTG GGC GGC CGC GAG CAG AAA CTG ATC TCT GAA GAA GAC CTG AAC TAC CCA

                                       150                                         180
TAC GAC GTC CCA GAC TAC GCT TAC CCA TAC GAC GTC CCA GAC TAC GCT TAC CCA TAC GAC

                                       210                                         240
GTC CCA GAC TAC GCT CCA AAT AAA GGA AGT GGA ACC ACT TCA GGT ACT ACC CGT CTT CTA

                                       270                                         300
TCT GGG CAC ACG TGT TTC ACG TTG ACA GGT TTG CTT GGG ACG CTA GTA ACC ATG GGC TTG

CTG ACT TAG GTA CC
```

Primer annotations: 7 (forward arrow over the start of line 1); 1 (starting at GCC, line 1, through CGC, line 2); 2 (reverse, line 2 through GCT, line 3); 3 (starting at TAC CCA, line 3, through AAA, line 4); 4 (reverse, CCA, line 4, through TGT, line 5); 5 (CTT CTA, line 4; GGG, line 5; through CC, line 6); 6 (reverse, ACC, line 5, through CC, line 6).

FIG. 6A

```
               10        20         30        40        50         60
CT  GCA GAT CGA TGA GCT CGC TAA CCA GCT GCC AGT GTG GTG GAA TTC GTC CTG AAC ATG AGC CTC CTC
                                                                             M   S   L   L

70        80         90         100       110        120       130
                                 *
CTC TCC TTC TAC CTG CTG GGG TTG CTT GTC AGT AGC GGG CAA GCT CTT CTT CAA GTG ACA ATT TCA
 L   S   F   Y   L   L   G   L   L   V   S   S   G   Q   A   L   L   Q   V   T   I   S

   140        150       160       170        180       190       200
                                                                    *
CTT AGC AAA GTA GAG CTT AGT GTT GGA GAA TCT AAA TTC TTC ACA TGT ACA GCG ATT GGT GAA CCT
 L   S   K   V   E   L   S   V   G   E   S   K   F   F   T   C   T   A   I   G   E   P

         210       220       230        240       250       260
GAA AGT ATA GAT TGG TAT AAT CCT CAA GGA GAG AAG ATA ATT TCA ACA CAG AGG GTA GTA GTG CAA
 E   S   I   D   W   Y   N   P   Q   G   E   K   I   I   S   T   Q   R   V   V   V   Q

  270       280       290        300       310       320        330
                                  *
AAG GAA GGT GTT AGG TCA CGG TTA ACC ATC TAC AAT GCA AAT ATA GAA GAT GCA GGG ATA TAT CGT
 K   E   G   V   R   S   R   L   T   I   Y   N   A   N   I   E   D   A   G   I   Y   R
```

FIG. 6B

```
      340                 350                 360                 370                 380                 390
TGT  CAA  GCA  ACA  GAT  GCC  AAA  GGA  CAA  ACA  CAA  GAA  GCT  ACA  GTA  GTT  TTG  GAA  ATT  TAC  CAA  AAA
 C    Q    A    T    D    A    K    G    Q    T    Q    E    A    T    V    V    L    E    I    Y    Q    K

400             410                 420                 430                 440                 450                 460
 *
CTC  ACT  TTC  AGA  GAA  GTG  GTA  TCT  CCA  CAA  GAA  TTC  AAA  CAA  GGA  GAA  GAT  GCA  GAA  GTG  GTT  TGC
 L    T    F    R    E    V    V    S    P    Q    E    F    K    Q    G    E    D    A    E    V    V    C

    470                 480                 490                 500                 510                 520                 530
                                                             *
CGA  GTT  AGC  AGT  TCA  CCT  GCA  CCT  GCT  GTC  AGC  TGG  TTG  TAT  CAT  AAT  GAG  GAA  GTC  ACC  ACT  ATT
 R    V    S    S    S    P    A    P    A    V    S    W    L    Y    H    N    E    E    V    T    T    I

          540                 550                 560                 570                 580                 590
TCC  GAC  AAT  CGG  TTC  GCT  ATG  TTA  GCA  AAC  AAT  AAC  CTG  CAG  ATT  CTC  AAC  ATC  AAT  AAA  AGT  GAT
 S    D    N    R    F    A    M    L    A    N    N    N    L    Q    I    L    N    I    N    K    S    D

  600                 610                 620                 630                 640                 650                 660
    *
GAA  GGT  ATA  TAC  AGA  TGT  GAA  GGA  AGA  GTG  GAG  GCC  AGG  GTA  GGC  GGC  CGC  GAG  CAG  AAA  CTG  ATT
 E    G    I    Y    R    C    E    G    R    V    E    A    R    V    G    G    R    E    Q    K    L    I
```

FIG. 6C

```
          670           680           690           700           710           720
                                                     *
TCT GAA GAA GAC CTG AAC TAT CCA TAC GAC GTC CCA GAC TAC GCT TAC CCA TAC GAC GTC CCA GAC
 S   E   E   D   L   N   Y   P   Y   D   V   P   D   Y   A   Y   P   Y   D   V   P   D

730           740           750           760           770           780           790
 TAC GCT TAC CCA TAC GAC GTC CCA GAC TAC GCT CCA AAT AAA GGA AGT GGA ACC ACT TCA GGT ACT
  Y   A   Y   P   Y   D   V   P   D   Y   A   P   N   K   G   S   G   T   T   S   G   T

    800           810           820           830           840           850           860
     *
ACC CGT CTT CTA TCT GGG CAC ACG TGT TTC ACG TTG ACA GGT TTG CTT GGG ACG CTA GTA ACC ATG
 T   R   L   L   S   G   N   T   C   F   T   L   T   G   L   L   G   T   L   V   T   M

          870           880           890           900           910           920
                                                     *
GGC TTG CTA ACT TAG GTA CCT TCT GAG GCG GAA AGA ACC AGC CGG ATC CCT CGA GGG ATC CAG ACA
 G   L   L   T   *

 930           940           950           960           970           980           990
TGA TAA GAT ACA TTG ATG AGT TTG GAC AAA CCA CAN CTA GAA TGC AGT GAA AAA AAT GCT TTA T
```

METHOD FOR ISOLATING AND DIRECTLY CLONING GENES WHICH ENCODE CELL-SURFACE AND SECRETED PROTEINS

FIELD OF THE INVENTION

This invention relates to cloning genes encoding cell surface and secreted proteins, and to obtaining such proteins by expression of such genes.

BACKGROUND OF THE INVENTION

Many clinically relevant proteins are found on cell surfaces or are secreted from cells. Such proteins include, but are not limited to, peptide hormones, cytokines, lymphokines, cell surface antigens, cell adhesion molecules (CAMs), and homing receptors. They represent a small percentage of all proteins synthesized by cells. Such proteins are usually identified initially on the basis of their activity, and then intensive scientific investigation must be carried out in an effort to isolate and characterize the proteins. Once such proteins are isolated, the genes encoding them may be isolated and cloned by a variety of methods for use in large-scale protein production. Such cloning methods require at least partially purified protein and additional information about the protein such as amino acid residue sequence, activity or antibodies specific for the protein.

In one cloning strategy, the protein is isolated, a partial amino acid residue sequence of the protein is determined, and a set of degenerate nucleic acid probes is designed based on the amino acid sequence. The probes are then used to screen DNA libraries. This approach is suitable for use where only small amounts of protein can be isolated to a high degree of purity, and where an amino acid sequence can be obtained. Where larger amounts of purified protein are available, antibodies to the protein may be made and used to screen so-called expression DNA libraries. These expression libraries utilize hybrid genes in which each cDNA is fused to a gene fragment encoding a signal peptide, so that the expressed protein is secreted by virtue of the exogenous signal peptide. The secreted proteins are then screened by the antibodies specific for the secreted protein. This approach may be suitable for use where the protein can be obtained in sufficient purity and amounts for obtaining antibodies.

DNA libraries are obtained either from the complete genomic DNA, a random fraction of the complete genomic DNA, or from cDNA derived from total cellular mRNA. Genes encoding cell surface and secreted proteins account for only a small fraction of genes encoding the bulk of proteins. Therefore, efforts at cloning cell surface and secreted proteins are laborious, time-consuming and not possible without having first obtained the protein or some knowledge about the protein.

SUMMARY OF THE INVENTION

This invention provides methods of cloning genes or fragments thereof encoding cell surface proteins and secreted proteins, without requiring any knowledge of the nature of the proteins encoded by the genes.

The invention features methods for directly cloning genes or gene fragments encoding cell surface proteins and secreted proteins, and vectors for use in the methods. Methods of the invention have been used to obtain novel genes, which are also encompassed by the invention.

In one general aspect, therefore, the invention features a method for directly cloning genes or gene fragments encoding cell surface proteins or secreted proteins, or fragments thereof, the method including steps of: obtaining a cDNA library, preferably by random priming; cloning the cDNA library into a DNA vector, described further herein, which includes a region encoding an identifiable marker or peptide and a membrane anchoring sequence; and monitoring expression of the identifiable peptide on the cell surface. The cDNAs are cloned into the vector in reading frame with the marker- and anchor-encoding region of the vector. Transcription of such of the cDNAs as contain signal peptide-encoding DNA results in appearance of the identifiable marker on the surface of the cell. As a result, DNA encoding cell surface proteins and secreted proteins (and amino-terminal fragments thereof) can be obtained directly. DNA fragments obtained by the method can be used by methods known in the art as probes to obtain the full-length gene.

In another general aspect, the invention features a DNA vector containing, in 5' to 3' order, a cloning site, a region encoding an identifiable peptide, and a region encoding a membrane anchoring domain, wherein the membrane anchoring domain may be or may include all or a portion of the identifiable marker. The vector additionally includes a genetic apparatus suitable for providing expression of a polypeptide cloned into the cloning site in a suitable host cell, such apparatus including, for example, a suitable promoter, stop codon, polyadenylation site, and the like.

In another general aspect, the invention features an expression system suitable for transfection with the vector and expression of the cloned gene or gene fragment.

In another general aspect, the invention features cDNAs and genes or gene fragments obtained by monitoring the appearance of the identifiable peptide on the surface of host cells obtained according to the method of the invention, and the proteins or protein fragments encoded thereby.

BRIEF DESCRIPTION OF THE DRAWINGS

FIG. 2 (SEQ ID NO:1 and SEQ ID NO:2) is a sequence listing for the supergene-x of FIG. 1, showing the nucleic acid sequence and the amino acid sequence encoded thereby.

FIG. 3 (SEQ ID NO:3) is the nucleotide sequence and restriction enzyme map of supergene-x.

FIG. 4 (SEQ ID NO:4) is a diagram of a primer map for the gene synthesis of supergene-x.

FIG. 6 (SEQ ID NO:5 and SEQ ID NO:6) is a sequence listing for clone 16f/1 showing the nucleic acid sequence and amino acid residues encoded thereby.

MODES OF CARRYING OUT THE INVENTION

Figure 1:
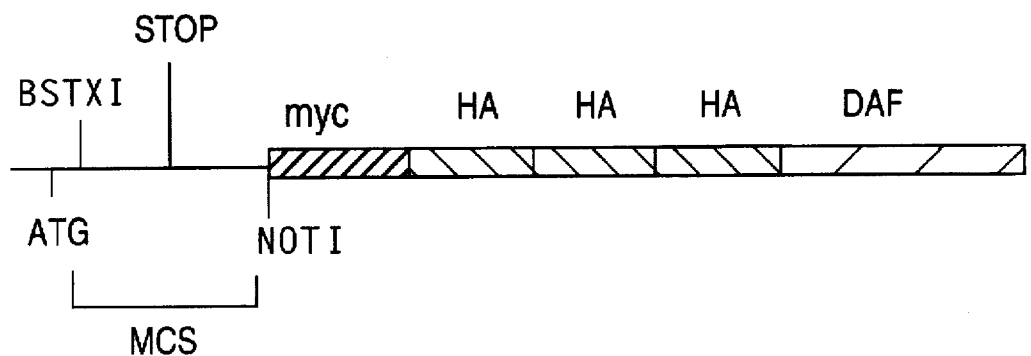
FIG. 1 is a diagram showing the structure of the supergene-x synthetic DNA sequence.

Proteins synthesized intracellularly may be transported to compartments within the cell, to the surface of the cell, or secreted to the extracellular milieu. In both prokaryotic and eukaryotic systems, which are considered to have similar mechanisms for protein translocation, proteins that are transported to the cell surface or are secreted must first be translocated across a hydrophobic membrane, their synthesis having been initiated in the hydrophilic cytoplasmic environment.

Virtually all cell surface and secreted proteins are expressed as precursors which contain an amino terminal extension, termed the signal peptide, ranging from 5 to 30 amino acid residues in length. The information required for initiation of the secretion process is thought to reside within the short signal peptide extension. The signal peptide is cleaved from the protein upon translocation across the membrane. Additionally, other hydrophobic regions within the protein, termed transmembrane (TM) domains, anchor cell surface proteins to cellular membranes.

The amino acid sequences of many signal peptides are known. Although there is little direct amino acid sequence homology among signal peptides, their overall structure is highly conserved, especially among prokaryotic signal peptides. The intracellular elements responsible for the eukaryotic signal peptide-induced secretion pathway have been well defined and facilitate translocation of the proteins across the endoplasmic reticulum (ER) membrane.

The present invention encompasses DNA cloning vectors, methods of use thereof and genes and peptides encoded thereby obtained by the methods. The preferred DNA vector is pSR-SG7 described herein, although any DNA vector containing the elements described herein is suitable for use in the present invention. Such vectors may be prepared by any means known in the art such as those discussed in *Molecular Cloning: A Laboratory Manual,* 2nd ed., Vols. 1–3, ed. Sambrook et al. (1989) Cold Spring Harbor Laboratory Press, or *Current Protocols in Molecular Biology,* ed. Ausubel et al., Greene Publishing and Wiley-Interscience: New York (1987 and periodic updates).

DNA vectors for expression of cell surface proteins, polypeptides, or fragments thereof, according to the invention, include any suitable vector into which has been cloned, 5' to 3', a cloning site, a region encoding a domain that includes an identifiable peptide domain and a membrane anchoring domain. In some embodiments, the membrane anchoring domain may include all or a portion of the identifiable peptide domain. The vector is constructed such that when a nucleotide encoding a signal peptide, or a functional portion thereof, is cloned into the cloning site in-frame with the region encoding the identifiable peptide, expression of the construct results in the appearance of the identifiable peptide on the cell surface. Thus, the cell expressing the hybrid gene can be identified by the presence of the identifiable polypeptide on its surface.

Methods of identifying peptides are known in the art and include, but are not limited to, immunological methods. For instance, an antibody recognizing the identifiable peptide can be used to identify a cell expressing the peptide under the control of a gene or gene fragment encoding a signal peptide. The antibody may be directly labeled or indirectly labeled via a second antibody or other chemical which contains a label and is specific for the first antibody. Suitable labels are known in the art and include, but are not limited to, fluorescent. Fluorescent labels are particularly preferred as they allow direct selection of labeled cells by fluorescence activated cell sorting. Alternatively, the antibody specific for the identifiable peptide may be directly or indirectly bound to a solid support to facilitate selection of the labeled cells.

Preferably, the vector contains a promoter 5' to the cloning site. Any promoter may be used, provided it allows expression in the expression system used. Suitable promoters include, but are not limited to, those obtained from cytomegalovirus (CMV), rous sarcoma virus (RSV), human immunodeficiency virus (HIV) long terminal repeat (LTR), and herpes simplex virus (HSV) thymidine kinase. Preferably, the promoter is the core SV40 early promoter. "R" and "U5" sequences which are located downstream of the transcription start site appear to be required for maximal expression from the HTLV-1 LTR. Fujisawa et al. (1986) *EMBO J.* 5:713–718; and Ohtani et al. (1987) *EMBO J.* 6:389–395. The fusion of the R sequence and part of the U5 sequence (R-U5) from the HTLV-1 LTR to the SV40 promoter-enhancer has been found to increase the expression level of proteins more than an order of magnitude over that from the original SV40 promoter-enhancer. Takebe et al. (1988) *Mol. Cell. Biol.* 8:466–472.

Examples of workable combinations of cell lines and expression vectors are described in Sambrook et al. (1989); Ausubel et al. (1987); and Metzger et al. (1988) *Nature* 334:31–36. Many useful vectors are known in the art and many are commercially available from various vendors. Suitable promoters for use in prokaryotic hosts include, but are not limited to, the trp, lac and phage promoters, tRNA promoters and glycolytic enzyme promoters. Useful yeast promoters include, but are not limited to, the promoter regions for metallothionein, 3-phosphoglycerate kinase or other glycolytic enzymes such as enolase or glyceraldehyde-3-phosphate dehydrogenase and the enzymes responsible for maltose and galactose utilization. Appropriate mammalian promoters include, but are not limited to, the early and late promoters from SV40 (Fiers et al. (1978) *Nature* 273:113) and promoters derived from murine Molony leukemia virus (MLV), mouse mammary tumor virus (MMTV), avian sarcoma viruses, adenovirus II, bovine papilloma virus and polyomas. In addition, the construct may be joined to an amplifiable gene so that multiple copies of the construct may be made. Amplifiable genes are known in the art and include, but are not limited to, the dihydrofolate reductase (DHFR) gene. For appropriate enhancer and other expression control sequences, see also *Enhancers and Eukaryotic Gene Expression,* Cold Spring Harbor Press: N.Y. (1983).

The vector may contain a start codon immediately 5' to the cloning site and a stop codon immediately 3' to the region encoding the membrane anchoring domain. The vector may contain signals including, but not limited to, a polyadenylation site 3' to the stop codon, and one or more enhancers. Any enhancer known in the art may be used. Suitable enhancers include, but are not limited to, the SV40 enhancer-promoter, the R-U5 segment of the HTLV-1 LTR, the CMV enhancer-promoter and any combination thereof. The CMV enhancer-promoter is described in Seed (1987) *Nature* 329:840–41. Preferably, the enhancer is the R-U5 segment of the HTLV-1 LTR and is 5' to the promoter.

In a preferred embodiment, the vector is a shuttle vector, capable of replicating in at least two unrelated expression systems. In order to facilitate such replication, the vector must contain at least two origins of replication, one effective in each expression system. Typically, shuttle vectors are capable of replicating in a eukaryotic expression system and a prokaryotic expression system. This enables detection of protein expression in the eukaryotic host (the expression cell type) and amplification of the vector in the prokaryotic host (the amplification cell type). Preferably, one origin of replication is derived from SV40 and one is derived from pBR322 although any suitable origin known in the art may be used provided it directs replication of the vector.

Preferably, the vector contains at least one gene encoding a selectable marker. Preferably, where the vector is a shuttle vector, there are at least two selectable markers encoded, one for the expression cell type and one for the amplification cell type. Any selectable marker known in the art may be used provided it functions in the expression system being utilized. Suitable selectable markers for mammalian expression systems include, but are not limited to, G418 resistance and methotrexate resistance. Typical selection genes are known in the art and include, but are not limited to, those which encode proteins that: (a) confer resistance to antibiotics or other toxic substances including, but not limited to, ampicillin, neomycin, methotrexate; (b) complement auxotrophic deficiencies; or (c) supply critical nutrients not available from complex media, such as the D-alanine racemase for Bacilli. The choice of the proper selectable marker depends on the host cell, and appropriate markers for various hosts are well known.

The cloning site is preferably a multicloning site to allow for cloning gene fragments in all three reading frames. Any multicloning site can be used, including many that are commercially available. To facilitate expression of the gene fragment cloned into the multicloning site, the site may also include an excisable stop codon to limit background expression.

The identifiable peptide may be any polypeptide known in the art for which there is a method of detection. Preferably, the polypeptide is antigenic and can be recognized by antibodies. More preferably, the identifiable polypeptide is one not ordinarily produced by the expression cell type or produced at only low levels. The identifiable peptide may comprise one or more identifiable domains. These domains may be antigenically distinct, tandem repeats of a single domain, or combinations thereof. Suitable identifiable peptides include, but are not limited to, influenza virus hemagglutinin (HA) and gp120 of HIV. Preferably the identifiable peptide is an antigenic region of HA, more preferably it is three tandem repeats thereof.

The membrane anchor domain may be any moiety capable of causing attachment to the cell surface. A variety of such moieties are known in the art and include, but are not limited to, transmembrane domains derived from known proteins, a span of hydrophobic amino acid residues sufficient to effect transmembrane spanning, an amino acid sequence that is targeted for post-translational modification by the covalent attachment of lipid molecules and polypeptides having sufficient affinity for a transmembrane protein to effect binding of the molecule to the surface of the cell membrane. Transmembrane domains, both natural and artificial, are known in the art and may be present in multiple copies separated by a sufficient number of amino acid residues to allow multiple membrane spanning by the domains. Typically, a transmembrane domain contains a number of hydrophobic amino acid residues sufficient to span a membrane, and includes at least one and usually several positively charged amino acid residues C-terminal to the hydrophobic amino acids. The positively charged amino acids prevent further transfer of the nascent protein through the membrane. Suitable membrane anchoring domains that function by lipid modification include, but are not limited to, the decay accelerating factor (DAF) which is modified by covalent linkage to glycosyl phosphatidyl inositol (GPI). Such are preferred embodiments and allow for subsequent specific cleavage of the protein from the cell surface. Suitable polypeptides having affinity for cell surface proteins include, but are not limited to, the HIV gp41 protein.

The DNA vectors of the present invention can be introduced into host cells by various methods known in the art. Such methods differ depending on the type of cellular host, and include, but are not limited to, electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al. (1989); and Ausubel et al. (1987). Reference herein to cells into which these DNA vectors have been introduced is intended also to include the progeny of such cells.

In another embodiment of the invention, the vector may contain a splice junction to increase stability and processing of mRNA in lukaryotic hosts. Preferably, the splice junction is 5' and adjacent to the region encoding the identifiable polypeptide. Any splice junction known in the art is suitable for use herein including, but not limited to, the XhoI-PstI segment of the SV40 late-gene splice junction.

An example of a vector according to the invention is the trapping vector, pSR-SG7, which was constructed by inserting a synthetic gene fragment, here termed supergene-x, into a eukaryotic expression vector, pSRα, described in Takebe et al. (1988). Supergene-x was inserted downstream of the enhancer and promoter, and upstream of the poly A sequence, as described more fully below.

Figure 5:
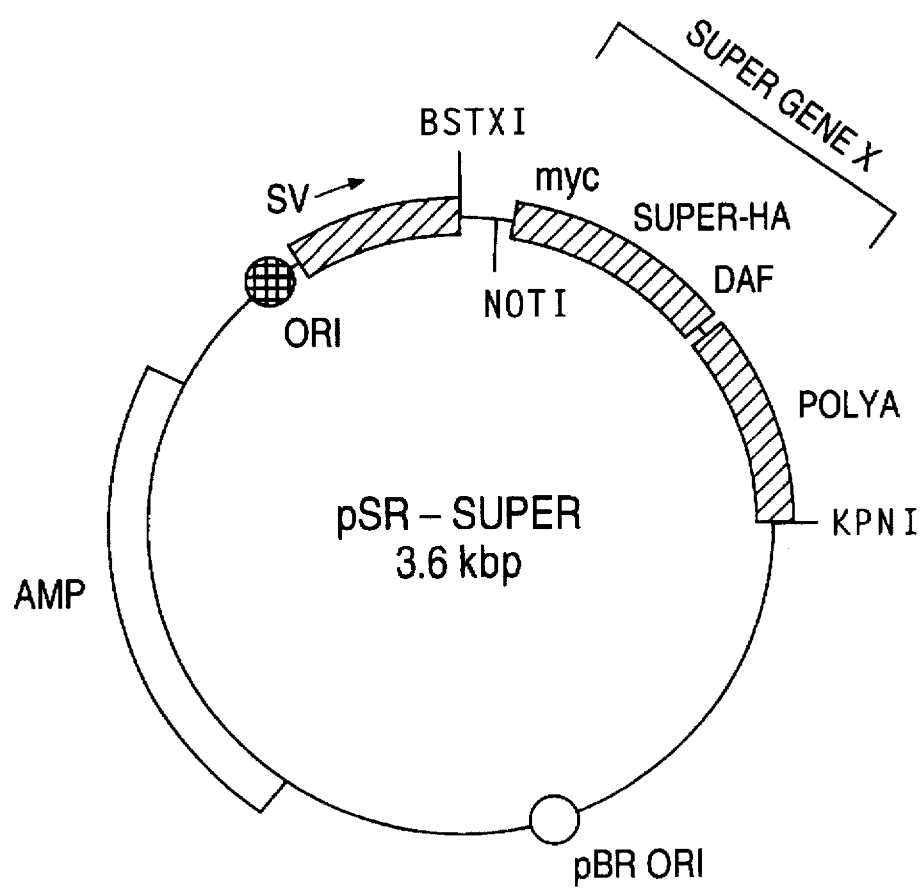
FIG. 5 is a diagram of the 3.6 kB pSR-SG7 vector.

Supergene-x, was first designed by arranging several DNA segments, including a multicloning site, a region encoding an identifiable peptide domain, and a region encoding a membrane anchor sequence into one common open-reading frame (ORF) to create an artificial gene designated supergene-x, as shown in FIG. 1. The DNA sequence for supergene-x was further analyzed by computer using a MicroGeni gene analysis program, to determine the coding sequence of supergene-x (FIG. 2) and to establish the restriction enzyme digestion map (FIG. 3). The important coding elements of supergene-x were arranged 5' to 3', as shown in FIG. 5.

Specifically, nucleotides 1 to 81 contain the multicloning site and include the restriction endonuclease sites shown in FIG. 3. Nucleotides 82 to 111 encode an 11 amino acid epitope of human c-myc protein, which is recognized by the monoclonal antibody (mAb) 9E10. Evan et al. (1985) *Mol. Cell. Biol.* 5:3610–2616. Nucleotides 116 to 195 encode three repeats of a 9 amino acid epitope from the influenza hemagglutinin (HA) protein, the domain of which is recognized by a variety mAbs, including, but not limited to, 12CA5. Wilson et al. (1984) *Cell* 37:767–778. Nucleotides 112 to 115 are a bridge to ensure that the myc domain and the three HA domains are translationally in-frame. Nucleotides 202 to 306 encode a 35 amino acid GPI linked membrane anchor derived from a DAF protein. Ferguson et al. (1988) *Ann. Rev. Biochem.* 57:285–320. Nucleotides 196 to 201 serve as an in-frame bridge. Nucleotides 307–314 encode an in-frame stop codon and a KpnI restriction endonuclease site.

The gene or gene fragments are preferably obtained from cDNA. The cDNA can be synthesized by any method known in the art; preferably it is randomly primed with primers that are linked to restriction endonuclease sites found in the vector. Random priming is preferred to poly d(T) priming as it has a greater probability of obtaining the 5' ends of genes which encode signal peptides. The cDNA fragments thus obtained are cloned into the vector which is then transfected into the expression host cell. In order to ensure that all the cells thus obtained contain the vector, the transfected cells may be selected for by the selectable marker. The cells are then separated on the basis of their expression of the identifiable peptide. This non-invasive procedure, preferably by FACS, selects cells transfected by vectors encoding and functionally expressing signal peptides. The vectors are then isolated from these cells and either subject to another round of selection based on expression of the identifiable peptide or, transfected into the amplification cell type. The transfected amplification cell type is then selected by the selectable marker, the vectors are purified and the cDNA sequence encoded thereby is sequenced by any method known in the art. If the sequence encodes a peptide fragment, the sequence may be used as a probe by methods known in the art to retrieve the entire gene.

The gene may then be recloned into any expression system known in the art. Expression systems are host/vector systems which can express a protein(s) from a nucleotide sequence cloned into the vector and transformed into an appropriate host cell. A wide variety of suitable expression systems are known in the art and are selected based on the host cells used, inducibility of expression desired and ease of use. Suitable vectors include, by way of example, the eukaryotic expression vector pSRα, described in Takebe et al. (1988) *Mol. Cell. Biol.* 8:466–472. The expression systems may be used to produce large amounts of the protein encoded by the cloned DNA.

Alternatively, the polypeptide may be chemically synthesized by any of various known methods, including, but not limited to, the phosphoramidite method described by Beaucage and Carruthers (1981) *Tetra. Letts.* 22:1859–62; and the triester method according to Matteucci et al. (1981) *J. Am. Chem. Soc.* 103:3185; preferably by use of a commercial automated synthesizer.

The expression and purification of proteins produced by the methods of the present invention is known in the art and includes, but is not limited to, those described, e.g., in Sambrook et al. (1989); and Ausubel et al. (1987). Suitable methods of purification include, but are not limited to, affinity chromatography, size exclusion chromatography, HPLC and FPLC. Any purification scheme that does not result in substantial degradation of the protein is suitable for use in the present invention.

Another aspect of the invention features the nucleotide sequence set out in FIG. 6 and the substantially purified protein obtained from expression of the DNA. The sequence was compared to known sequences and found to be novel with homology to neural cell adhesion molecules (NCAMs).

NCAMs are members of the immunoglobulin superfamily, mediating homophilic and heterophilic cell to cell interactions. NCAMs appear in various isoforms generated by alternative splicing. Hemperly et al. (1986) *Proc. Natl. Acad. Sci. USA* 83:3037–41; Barthels et al. (1987) *EMBO J.* 6:907–14; and Barthels et al. (1992) *Eur. J. Neurosci.* 4:327–337. During embryonic development, NCAMs are expressed in derivatives of all three germ layers whereas in the adult animal they are predominantly present in neural tissue. Processes like neurulation, axonal outgrowth, histogenesis of the retina and development of the olfactory system are correlated with the regulated expression of NCAMs. Crossin et al. (1990) *Exp. Neurol.* 109:5–15; Tosney et al. (1986) *Dev. Biol.* 114:437–52; Thiery et al. (1977) *J. Biol. Chem.* 252:6841–45; Key et al. (1990) *J. Cell Biol.* 110:1729–43; and Edelman (1988) *Biochem.* 27:3534–43.

Additionally, the DNA compositions of the present invention may be chemically or biochemically modified or contain non-natural or derivatized nucleotide bases. Nucleic acids encoding the polypeptides of the present invention include not only the native or wild-type sequences, but also any sequence that is capable of encoding the desired polypeptide. The nucleotide sequences include modifications such as deletions, substitutions and additions particularly in the noncoding regions. Such changes are useful to facilitate cloning and modify gene expression.

Various substitutions can be made in the coding region that either do not alter the amino acids encoded or result in conservative changes. These substitutions are encompassed by the present invention. Conservative amino acid substitutions include substitutions within the following groups: glycine, alanine; valine, isoleucine, leucine; aspattic acid, glutamic acid; asparagine, glutamine; serine, threonine; lysine, arginine; and phenylalanine, tyrosine. While conservative substitutions do effectively change one or more amino acid residues contained in the polypeptide to be produced, the substitutions are not expected to interfere with the biochemical activity of the polypeptide to be produced. Nucleotide substitutions that do not alter the amino acid residues encoded are useful for optimizing gene expression in different systems. Suitable substitutions are known to those of skill in the art and are made, for instance, to reflect preferred codon usage in the expression systems.

As noted above, the invention features proteins, peptides, polypeptides and fragments thereof, that are naturally found on the cell surface or are secreted from the cell. The invention also includes homologs of such proteins and polypeptides or fragments, and nucleic acid sequences encoding such homologs. A polynucleotide or fragment thereof is "substantially homologous" (or "substantially similar") to another, as those terms are used herein, if, when optimally aligned (including any appropriate nucleotide insertions or deletions) with another polynucleotide (or its complementary strand), there is substantial nucleotide sequence identity, preferably at least about 90%, and more preferably at least about 95 to 98% of the nucleotide bases. Homology also exists between polynucleotides or fragments thereof if one hybridizes to the other under selective hybridization conditions. Kanehisa (1984) *Nucl. Acids Res.* 12:203–212.

Another aspect of the invention features useful compositions that include the nucleotides and polypeptides shown in FIG. 6. Such compositions may be useful, for example, in methods of treatment or screening or diagnosis of disease. For instance, compositions thereof may contain the substantially purified polypeptides and physiologically acceptable buffers for administration for therapeutic use.

Suitable buffers and methods of administration are known in the art. The effective concentrations of the polypeptides will need to be determined empirically and will depend on the type and severity of the condition being treated and the health of the patient. Such determinations are within the skill of one in the art. Moreover, these are human polypeptides the administration of which is not likely to induce reactions such as anaphylactic shock or the production of antibodies. The upper concentration of these polypeptides for therapeutic use is thus not limited by these physiologic considerations.

The following examples are meant to illustrate but not limit the claimed invention.

EXAMPLES

Example 1

Construction of the pSR-SG7 Vector and Supergene-x

Supergene-x was generated using polymerase chain reaction (PCR) techniques according to the method described by Mullis et al. (1986) *Quant. Biol.* 51:263–273, using eight overlapping primers made from the supergene-x DNA sequence. FIG. 4 illustrates the primers used for the synthesis of supergene-x. Briefly, the PCR reaction was performed in a buffer containing 50 mM KCl, 10 mM Tris-HCl (pH 8.3), 2.5 mM $MgCl_2$, 0.01% (w/v) gelatin, 250 μM each dNTP, 10 μM each of primer 1 (1–81), primer 2 (141–61), primer 3 (123–203), primer 4 (253–183), primer 5 (233–314), and primer 6 (314–289) and 2 units of Taq polymerase. The reaction mixture was denatured at 94° C. for 45 seconds and annealed at 55° C. for 45 seconds. Thereafter, the chain polymerization was performed at 72° C. for 1.5 minutes. After 25 cycles, 1 μL of the reaction mixture was further amplified by two short primers, primer 7 (1–21) and primer 6 (314–289) for an additional 30 cycles. The resulting 314 nucleotide supergene-x fragments were digested with KpnI and PstI, and further purified by GeneClean II Kit (Bio101), according to the manufacturer's instructions. The purified fragment was later cloned into the PstI and KpnI-digested vector pSRα to form pSRα•SG7.

The pSRα•SG7 constructs were transformed into the Epicurian coli® XLI Blue strain of *Escherichia coli* (Stratagene). The transformation was performed according to the method described by Hanahan (1983) *J. Mol. Biol.* 166:557–80. The transformed constructs were then spread onto ampicillin-containing plates. Minipreps of the constructs were prepared from the resulting ampicillin resistant colonies using the Magic™ Minipreps DNA purification system kit obtained from Promega according to the manufacturer's instructions. Based on the initial restriction enzyme analysis, four clones of the construct were selected for DNA sequence determination of the supergene-x region of the construct. Sequenase® Version 2.0 DNA Sequence Kit (United States Biochemical Corp.) was used to determine the sequence of the four clones and the dideoxy DNA sequencing was performed essentially according to the manufacturer's instructions. Based on the DNA sequence analysis of the construct, clone #7 was chosen for subsequent use and was designated pSR-SG7. The DNA sequence obtained and the amino acid sequence encoded by the supergene-x region of pSR-SG7 is displayed in FIG. 2. The construct obtained is shown in FIG. 5.

Example 2

Pilot Study Comparing the Localization of Supergene-x Fusion Products with Known Genes with and without Signal Peptide Encoding Regions A pilot study was designed to demonstrate that: (1) gene fragments linked in-frame 5' to supergene-x in the pSR-SG7 construct are properly expressed in vivo; (2) those gene fragments that encode signal peptides cause the supergene-x fusion products to be localized to the cell surface membranes; and (3) those gene fragments which do not encode signal peptides cause the supergene-x fusion products to remain sequestered within the cells. The genes encoding: human FLK-2 (hFLK-2), a cell-surface receptor containing a signal peptide; mouse Steel Factor (mSLF), a secreted protein containing a signal peptide; and human cdk2 (hcdk2), a cytoplasmic and nuclear protein which lacks a signal peptide, were separately cloned into pSR-SG7. For each gene tested, a NotI restriction endonuclease linker was ligated to the 3' end of the cDNA such that the gene was linked in-frame with supergene-x when cloned into pSR-SG7. In addition, in the case of hFLK-2, the portion of the hFLK-2 gene which encodes the carboxy-terminal transmembrane (TM) domain, which is used to anchor molecules onto the cell surface, was excised prior to the addition of the NotI linker, thus allowing transport of the encoded protein across the cell membrane and subsequent anchorage in the membrane by the supergene-x encoded DAF. The cDNAs for the three genes tested were excised with either PstI and NotI restriction endonucleases or with NheI and NotI, as described more fully below. The resulting cDNA fragments were ligated into pSR-SG7 digested with either PstI and NotI or NheI and NotI. Because of the positions of the restriction sites in the hFLK-2, mSLF, and hcdk2 cDNA fragments and in pSR-SG7, the three genes were all ligated into their respective pSR-SG7 vectors in the proper orientation and were transcribed from the Simian Virus 40 (SV40) promoter of pSR-SG7 in-frame and contiguous with the supergene-x region of the constructs.

Ligation of hFLK-2, mSLF, and hCDK-2 into pSR-SG7

The Plasmid Sources.

The full-length hFLK-2 (human FLK-2) cDNA clone was isolated by using a probe comprised of a murine FLK-2 cDNA fragment as described by Matthews et al. (1991) *Cell* 65:1143–1152. The probe was used to screen a human fetal stem cell population Zap cDNA library prepared as follows. Briefly, $10^7$ human fetal bone marrow stem cells ($CD34^+$ $thy^+lin^-$) were isolated by the method described by Baum et al. (1992) *Proc. Natl. Acad. Sci.* USA 89:2804–2808. A lambda Zap cDNA library was constructed with mRNAs derived from these cells by a cDNA library construction kit according to the manufacturer's instructions (Lambda Zap II kit, Stratagene). The hFLK-2 molecule is a cell surface tyrosine kinase receptor and shares an overall 89% homology to its murine counterpart. Recently, Rosnet et al. (1993) *Blood* 82:1110–1119 reported cloning human FLT3/FLK2 cDNA and the full-length cDNA clone sequence has been published. The sequence used herein is the same as that published by Rosnet et al. (1993)

The secreted form of murine steel factor (mSLF) gene was cloned using PCR with amplification primers synthesized according to the published mSLF gene sequence. Anderson et al. (1990) *Cell* 63:235–243.

Briefly, mRNA was isolated from AC6.21 mouse stromal cells by the method described by Chirgwin et al. (1986) *Biochem.* 18:5294. RT-PCR was performed with the mSLF specific primers described below, essentially according to the method described by Veres et al. (1987) *Science* 237:415–417.

The hcdk-2 gene was provided by Dr. D. Morgan, University of California San Francisco. The gene Sequence has been published. Gu et al. (1992) *EMBO J.* 11:3995–4005; and Tsai et al. (1991) *Nature* 353:174–177.

The Cloning Strategy

In order to fuse the portion of the hFLK-2 gene encoding the cell surface domain in-frame with supergene-x, a pair of nested primers was synthesized and used to amplify the desired region. The 5' primer flanked the NheI restriction endonuclease site and the N-terminal amino acid residues of hFLK-2 and has the following nucleotide sequence:

5' CTCGCTAGCCAATGCCGGCGTTG-GCGCGCGACGGC 3' (SEQ ID NO:7). The 3' primer flanked the NotI site on its 5' end and encodes 7 amino acids N-terminal to the TM domain of hFLK-2 and has the following nucleotide sequence:

5' CTCGCGGCCGCGTTGTCTTGGAT-GAAAGGGAAG 3' (SEQ ID NO:8). The PCR reaction was performed in a Perkin-Elmer Cetus instrument (DNA thermal cycler 480) for 30 cycles according to the manufacturer's instructions. The reaction mixture contained 1 pg of hFLK-2 cDNA, 20 pmol of each primer, 20 mM Tris-HCl (pH 8.3), 1.5 mM $MgCl_2$, 25 mM KCl, 0.05% Tween 20, 25 μM each dNTP and 2 units of Taq DNA polymerase. The PCR cycle profile included: denaturation at 94° C. for 45 seconds; primer annealing at 55° C. for 45 seconds; primer extension at 72° C., for 2.5 minutes. The resulting 1.5 kb hFLK-2 DNA fragment was isolated and digested with NheI and NotI. The digested DNA was then ligated into NheI and NotI digested pSR-SG7 to produce pSR-SG7-hFLK-2.

In order to fuse the mSLF gene in-frame with supergene-x, a pair of nested primers was synthesized and used to amplify the desired region. The 5' primer DNA sequence has the following nucleotide sequence:

5' CTGTACGGAAGTGTTACTTCTGCTC 3' (SEQ ID NO:9). Since the mSLF cDNA was cloned into pSRα vector, the primer sequence shown here is the 5' flanking sequence of the vector. The 3' primer sequence flanked the NotI site on its 5' end and has the following nucleotide sequence:

5' CTCGCGGCCGCTGGCTGCAACAGGAGG-TAACATAAATG 3' (SEQ ID NO:10). The PCR reaction was performed in a Perkin-Elmer Cetus instrument (DNA thermal cycler 480) for 30 cycles according to the manufacturer's instructions. The reaction mixture contained 1 pg of mSLF cDNA, 20 pmol each primer, 20 mM Tris-HCl (pH 8.3), 1.5 mM $MgCl_2$, 25 mM KCl, 0.05% Tween 20, 25 μM each dNTP, 2 units of Taq DNA polymerase. The PCR cycle profile included denaturation at 94° C. for 45 seconds, primer annealing at 55° C. for 45 seconds and primer extension at 72° C. for 1.5 minutes. The resulting 0.6 kB mSLF DNA fragment was isolated and digested with PstI and NotI. The digested DNA fragment was later ligated into PstI and NotI digested pSR-SG7 to produce pSR-SG7•mSLF.

The hcdk-2 gene was fused with supergene-x in a similar manner except the amplification primers were different. The 5' primer for hcdk-2 has the following nucleotide sequence:

5' CTTCTGCAGGGTTCCCAG 3' (SEQ ID NO:11) and the 3' primer has the following nucleotide sequence:

5' CTCGCGGCCGCTCCGTCCATCTTCATCCAG 3' (SEQ ID NO:12). The 1.35 kb amplified hcdk-2 fragment was digested with PstI and NotI and subcloned into PstI and NotI digested pSR-SG7 to produce pSR-SG7•hcdk-2.

The resulting pSR-SG7•hFLK-2, pSR-SG7•mSLF, and pSR-SG7•hcdk2 constructs were each then transfected into cos cells according to the DEAE-dextran method described by Kaufman (1990) *Met. Enzymol.* 185:487–511. Localization of the three supergene-x fusion proteins was analyzed by both immunofluorescent microscopy and GPI-PLC cleavage experiments as described below.

Immunofluorescent Microscopy

(1) Preparations to Analyze Transfected Cos Cells for Cell Surface Expression of the Supergene-x Fusion Proteins Cos cells transfected with the pSR-SG7•hFLK-2, pSR-SG7•mSLF or pSR-SG7•hcdk2 constructs were detached from the culture dishes by treatment with 0.3% ethylenediaminetetraacetic acid (EDTA) in phosphate buffered saline (PBS). The cos cells were washed once in PBS containing 2% fetal calf serum (FCS), 0.01% EDTA and 0.001% sodium azide. Thereafter the cos cells were incubated with 12CA5 antibodies (BABCO, Berkeley, Calif., or Bochrinder Mannheim) at a final concentration of 0.5 μg/mL for 45 minutes. The cells were washed again as before and stained with FITC-conjugated goat anti-mouse IgG antibodies. The cells were washed as before and applied to a microscope slide.

(2) Analysis of the Transfected Cos Cells for Intracellular Expression of the Supergene-x Fusion Proteins Cos cells transfected with the pSR-SG7•hFLK-2, pSR-SG7•mSLF, and pSR-SG7•hcdk2 constructs were grown on microscope cover slips overnight at 37° C. in DMEM medium containing 10% FCS with 5% $CO_2$. The cells were fixed on the surface of the cover slips by treatment with a solution consisting of 50% ethanol and 50% acetone. The cover slips were removed from the fixing solution and washed with PBS and 2% FCS. The cells on the cover slips were stained with 12CA5 antibodies for 30 minutes at room temperature. The cells were washed again as before and stained with FITC-conjugated goat anti-mouse IgG antibodies. Finally the cells were stained with propidium iodide (PI) in order to visualize their nuclei. The PI staining solution was made in PBS at a PI concentration of 1 pg/mL, and applied to the cells for a period of 10 minutes at room temperature. Thereafter the cells were washed once with PBS.

(3) Preparation of Immunofluorescent Micrographs of FITC-stained Cos Cells

A Nikon Labophot-2 was used at a magnification of from 40× to about 100×. The ultraviolet light source was generated by a Nikon EF-P Mercury set. For the FITC, a UV filter with an excitation range of Ex 330 to 380 or Ex 470 to 490 was used. Photography was done using a Nikon UFX-DX computerized photosystem using Kodak Ektachrome 400HC film.

Immunofluorescent micrographs of pSR-SG7•hFLK-2, pSR-SG7•mSLF, and pSR-SG7•hcdk2 transfected cos cells stained with FITC-conjugated antibodies as described above were obtained. The results obtained are summarized in Table 1, where SP is signal peptide.

TABLE 1

| | | supergene-x expression | | |
|---|---|---|---|---|
| protein type | pSR-SG7 | intracellular expression | cell surface expression | SP |
| cell surface | hFLK-2 | + | + | + |
| secretory | mSLF | + | + | + |
| nuclear | hcdk2 | + | − | − |

The results show that mSLF, a secretory protein, hFLK-2, a cell surface protein, when fused with supergene-x result in correct expression of mSLF and hFLK on the cell surface by virtue of their signal peptide sequences. In contrast, hcdk2, a nuclear protein, was targeted to the nucleus when fused to supergene-x. Notably, hcdk2 was not expressed on the cell surface even though the fusion protein Contains cell surface anchoring sequences.

GPI-PLC Cleavage of DAF-Anchored Supergene-x Fusion Products from the Exterior of Plasma Membranes Samples of both pSR-SG7•mSLF and pSR-SG7•hcdk2 transfected cos cells were each divided into three aliquots of approximately $2\times10^6$ cells each. The first aliquot of each cell type was lysed by adding 100 μL of a lysis buffer containing 0.1% of Triton X-100, 150 mM NaCl, 20 mM Tris-HCl at a pH of 7.6. The cells and lysis buffer mixture were maintained for 10 minutes on ice and then centrifuged for 10 minutes at 3000×g to remove the cell debris. Thereafter, the supernatant was transferred to a new tube and an equal volume of 2× sample buffer was added. 2× sample buffer is 0.06M Tris-HCl, pH 6.8, 2% SDS, 10% glycerol and 0.025% Bromophenol Blue.

The second aliquot of each cell type was incubated with 0.1 U/mL glycosyl-phosphatidyl inositol phospholipase C (PI-PLC, ICN) in PBS ($5\times10^6$/mL) at 37° C. for 1 hour. After the treatment, the cells were sedimented and the supernatant was transferred to a new tube containing an equal volume of 2× sample buffer.

The third aliquot of each cell type was treated in the same manner as the second aliquot, except that instead of being incubated with PI-PLC, the cells were treated with PBS. The samples were then heated at 85° C. and loaded onto a 4–20% gradient for SDS gel electrophoresis under 200 volts for 1 hour in a miniprotein gel device (Xcell, from Novell Experimental Technology, Inc.). After electrophoresis, the gel was soaked in electroblotting buffer containing 20 mM Tris/150 mM glycine, PH 8.0, for 15 minutes and then assembled into a Western electroblotting (semi-dry) apparatus with a nitrocellulose filter according to the manufacturer's instructions (Novell Experimental Technology). The proteins were transferred onto a nitrocellulose filter under conditions of 150 mA constant current for 1 hour in an electroblotting buffer.

After blotting, the HA tagged protein detection was performed using the ProtoBlot® Western Blot AP Systems Kit according to the manufacturer's instructions (Promega). Briefly, the nitrocellulose filter was first blocked with 2% BSA in TBS (Tris buffered saline: 150 mM NaCl, 20 mM Tris pH 7.4, 0.2% Tween, and 1 mM EDTA) for 1 hour at room temperature. The mAb 12CA5 was diluted to 0.005 μg/mL to stain the HA tagged protein using the same blocking solution for 45 minutes at room temperature. After washing twice with TBS, the 12CA5 stained filter was further incubated with goat anti-mouse Ig-AP conjugates (Promega) at a concentration of 0.02 μg/mL. The AP color reaction was performed according to the manufacturer's instructions using reagents from the Promega kit.

The results obtained indicate that both the mSLF and hcdk2 supergene-x fusion proteins were found in the cell lysate samples, demonstrating that both fusion proteins are properly expressed. However, only the mSLF fusion protein, and not the hcdk2 fusion protein, was found in the supernatant samples with or without GPI-PLC treatment indicating the mSLF fusion protein was expressed on the cell surface via GPI anchoring. It has been shown that GPI anchored protein on cell surfaces can be continuously shed into the medium or supernatant. Ferguson (1988) *Ann. Rev. Biochem.* 57:285–320. Furthermore, the mSLF fusion protein was found to be substantially more abundant in the GPI-PLC treated supernatant sample than the PBS treated sample demonstrating that a significant fraction of the extracellular mSLF fusion protein was anchored via GPI to the surface of the plasma membrane and can be released by GPI-PLC into the medium. Therefore, the insertion of a signal peptide encoding gene fragment into the 5' coding region of pSR-SG7 causes the resulting fusion protein to be preferentially localized and anchored to the exterior of the plasma membrane whereas insertion of a gene fragment lacking a signal peptide encoding region results in expression of an intra-cellular protein.

Example 3

Construction of pSR-SG7•cDNA Library cDNA was prepared from both 1 μg of mRNA derived from human brain tissue and 1 μg of mRNA derived from human placental tissue in separate, parallel reactions. The mRNA for human brain tissue and placental tissue were purchased from Clontech. The cDNA was prepared using a Copy Kit II (Invitrogen) according to the manufacturer's instructions. First strand cDNA synthesis was initiated with DNA primers, consisting of random sequence, nine nucleotide oligomers covalently attached to EcoRI-NotI linkers. A random primer, as opposed to a poly-dA primer, was used in order to enrich for 5' gene sequences in the cDNA population, since signal peptides are encoded within the first 400 bases from the 5' end of mRNA. Sabatini et al. (1982) *J. Cell Biol.* 92:1–22. Following cDNA synthesis, BstXI restriction endonuclease linkers were ligated onto the cDNA fragments.

The cDNA fragments of greater than 400 base pairs were isolated by a Chromaspin column 400 (Clontech) and excised with BstXI and NotI. The resulting BstXI-NotI cDNA fragments were ligated into pSR-SG7 digested with BstXI and NotI. The positions of the BstXI and NotI restriction sites in the cDNA and the pSR-SG7 vector allowed ligation of the genes from the cDNA library to be in a single orientation, in-frame and contiguous with the attached supergene-x region of the constructs. The resulting pSR-SG7•cDNA constructs were transformed into *E. coli* K-12 strain DH5α according to the method described by Hanahan (1983). The transformations generated approximately 30 thousand unamplified colonies each for the brain and placenta derived libraries. The transformed DH5α colonies from the libraries were then pooled. A maxiprep of the pSR-SG7•cDNA constructs was prepared from the pooled library using the Magic™ Maxiprep Kit (Promega) according to the manufacturer's instructions.

Example 4

Isolation of a Novel Human Gene Fragment Encoding a Protein with a Signal Peptide The pSR-SG7•cDNA library obtained according to the method described in Example 3 was transfected into cos cells using the DEAE-dextran method (Warren and Shields, 1984).

In order to enrich the transfected cos cell population for cells expressing gene fragments encoding signal peptides within the pSR-SG7 vectors, magnetic bead separation was employed to select cells expressing HA antigen on their plasma membranes. The cells were detached from the culture dishes by treatment with 0.3% EDTA in PBS for 15 minutes, and incubated with the anti-HA antibody, 12CA5 at a concentration of 0.5 μg/mL, according to the method described by Wilson et al. (1984) *Cell* 37:767–778. The 12CA5-labeled cos cells were mixed with a suspension of Dynal magnetic beads coated with a goat anti-mouse IgG antibody available from Dynal, Inc. Dynabeads M-450 goat anti-mouse Ig were washed once with PBS containing 2% FCS plus 0.001% sodium azide and resuspended in the same washing solution at a bead concentration of $10^8$/mL. The washed beads used for cell separation were $10^6$ beads for $10^6$ cells, at 4° C. for 1 hour. The rest of the separation method followed the manufacturer's instructions. The culture tubes were placed in a magnetic stand, causing the beads and their associated cells to collect on the sides of the tubes. The non-bound cells were then removed.

The bead-bound cells were subjected to Hirt DNA extraction. Hirt (1967) *J. Mol. Biol.* 26:365–369. The resulting pSR-SG7•cDNA constructs were transformed into DH5α as described above, and the transformed DH5α colonies were pooled. A maxiprep of the pSR-SG7•cDNA constructs was prepared from the pooled DH5α library and retransfected into cos cells as described above. The magnetic bead separation, the passage through DH5α, and the transfection into cos cells were repeated a total of three times. After the third round of 12CA5 conjugated bead selection, Hirt extracted DNA from 12CA5 positive cell pellets were transformed into DH5α and 40 bacterial colonies were picked. Miniprep DNAs for each bacterial colony were prepared and transfected into cos 7 cells separately. The 12CA5 positive cDNA clones were identified by a fluorescent microscope screening method with a goat anti-mouse Ig-FITC conjugated. The positive cDNA clones were subjected to DNA sequencing. The DNA sequences obtained were compared to known protein sequences using the Genbank database. The DNA sequences and corresponding amino acid sequences for a novel gene fragment is shown in FIG. 6. FIG. 6 shows the nucleic and amino acid sequences of clone 16f/1. Clone 16f/1 was found to have substantial homology to neural cell adhesion molecule (NCAM) and thus represents a novel NCAM gene.

Example 5

Gene fragments obtained as described above are used to obtain the gene encoding the full length protein. Nucleic acid probes and primers are prepared using standard techniques. Such a probe or primer comprises an isolated nucleic acid. In the case of probes, the nucleic acid further comprises a label (e.g., a radionuclide such as $^{32}P$ or $^{35}S$) or a reporter molecule (e.g., a ligand such as biotin, or an enzyme such as horseradish peroxidase). The preparation and use of probes and primers is described in Sambrook et al. (1989) and Ausubel et al. (1987). Subsequent subcloning and expression of the full-length genes is by any method known in the art.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

I claim:

1. A composition comprising a DNA vector comprising, 5' to 3':

a) a cloning site b) a region encoding an identifiable peptide; and c) a region encoding a membrane anchoring domain;

wherein the identifiable peptide may also be the membrane anchoring domain, further wherein, upon cloning of a nucleotide encoding a signal peptide, or a functional portion thereof, in-frame with the region encoding the identifiable peptide, expression thereof results in appearance of the identifiable peptide on a cell surface.

2. The vector according to claim 1, further comprising a promoter 5' to the cloning site.

3. The vector according to claim 1, further comprising a start codon immediately 5' to the cloning site.

4. The vector according to claim 1, further comprising a stop codon immediately 3' to the region encoding the membrane anchoring domain.

5. The vector according to claim 1, further comprising at least one enhancer.

6. The vector according to claim 1, wherein there are at least two origins of replication, wherein at least one first origin facilitates replication in an expression cell type, and at least one second origin facilitates replication in an amplification cell type.

7. The vector according to claim 1, further comprising at least one gene encoding a selectable marker.

8. The vector according to claim 1, wherein the cloning site is a multiple cloning site.

9. The vector according to claim 1, wherein at least one nucleotide is added or subtracted to the cloning site to facilitate the expression of gene fragments in multiple reading frames.

10. The vector according to claim 1, wherein the membrane anchoring domain includes the identifiable peptide.

11. The vector according to claim 1, wherein the identifiable peptide is antigenic.

12. The vector according to claim 1, wherein the membrane anchoring domain is selected from the group consisting of one or more transmembrane domains, a sequence of hydrophobic amino acid residues sufficient to effect transmembrane spanning, a sequence of amino acid residues targeted for post-translational modification by the covalent attachment of lipid molecules, and a polypeptide having sufficient affinity to a cell surface protein to effect binding of the molecule to the surface of the cell membrane.

13. The vector according to claim 1, further comprising a splice junction.

14. The vector according to claim 2, wherein the promoter is selected from the group consisting of those obtained from cytomegalovirus (CMV), rous sarcoma virus (RSV), human immunodeficiency virus (HIV) long terminal repeat (LTR), simian virus 40 (SV40), and herpes simplex virus (HSV) thymidine kinase.

15. The vector according to claim 4, further comprising a polyadenylation signal 3' to the stop codon.

16. The vector according to claim 5, wherein the enhancer is selected from the group consisting of the SV40 enhancer-promoter, the R-U5 segment of the human T cell lymphotropic virus-1 (HTLV-1) LTR, and the CMV enhancer-promoter.

17. The vector according to claim 6, wherein the expression cell type is eukaryotic and the amplification cell type is prokaryotic.

18. The vector according to claim 17, wherein the origins of replication are derived from SV40 and pBR322.

19. The vector according to claim 7, wherein the at least one selectable marker facilitates selection in an expression cell type.

20. The vector according to claim 7, wherein the at least one selectable marker facilitates selection in an amplification cell type.

21. The vector according to claim 8, wherein the multiple cloning site contains an excisable stop codon.

22. The vector according to claim 10, wherein the vector comprises nucleotides encoding one or more identifiable peptides wherein there are either one or more copies of the same peptide or different peptides.

23. The vector according to claim 10, wherein the identifiable peptide is selected from antigenic portions of the group consisting of influenza virus hemagglutinin and human immunodeficiency virus gp120.

24. The vector according to claim 23, wherein the region encoding the identifiable peptide encodes at least three repeats of an antigenic portion the influenza virus hemagglutinin.

25. The vector according to claim 12, wherein the membrane anchoring domain comprises an amino acid residue sequence targeted for post-translational modification by the covalent linkage of glycosyl-phosphatidyl inositol-like structures or isoprenoids.

26. The vector according to claim 25, wherein the membrane anchoring domain comprises a functional portion of a decay accelerating factor.

27. The vector according to claim 13, wherein the splice junction is 5' and adjacent to the region encoding the identifiable peptide.

28. The vector according to claim 27, wherein the splice junction is a copy of the SV40 late-gene splice junction.

29. A method of isolating nucleotides encoding peptides comprising signal peptides, or functional portions thereof, comprising the steps of:

a) obtaining a collection of gene fragments;

b) cloning the gene fragments into the cloning site of the vector according to claim 1;

c) transfecting the product of step b) into an expression cell;

d) incubating the transfected cells under conditions and for a time sufficient for expression of the gene fragment; and e) selecting transfected cells that contain the identifiable peptide on the cell surface.

30. The method according to claim 29, wherein the gene fragments comprise cDNA.

31. The method according to claim 29, wherein the gene fragments comprise genomic DNA.

32. The method according to claim 29, wherein the cells are selected by antibodies that recognize the identifiable peptide.

33. The method according to claim 29, wherein the step of selecting cells is performed at least once and is selected from the group consisting of immunoaffinity column chromatography, panning, magnetic bead immunoaffinity, and fluorescence activated cell sorting.

34. The method according to claim 29, wherein the cells are selected at least once by exposing the cells to an antibody-conjugated stain or indicator, which antibody binds to the identifiable peptide and monitoring the presence of the antibody.

35. The method according to claim 29, wherein the selecting cells step further comprises selecting for cells containing a vector by adding a selection agent which selects for a selectable marker on the vector.

36. The method according to claim 29, further comprising amplifying the vector by at least once by passage through an amplification cell type.

37. The method according to claim 30, wherein synthesis of the cDNA is initiated from a primer comprising a poly (dT) sequence.

38. The method according to claim 30, wherein synthesis of the cDNA is initiated from at least one primer comprising a sequence of random nucleotides.

39. The method according to claim 30, wherein synthesis of the cDNA is initiated from a primer comprising at least one restriction endonuclease site.

40. The method according to claim 30, wherein a primer comprising at least one restriction endonuclease site is used to initiate cDNA synthesis and further comprising the step of ligating linkers comprising at least one restriction endonuclease site to the cDNA fragments.

41. The method according to claim 38, wherein the at least one primer comprises a sequence of at least nine random nucleotides.

42. The method according to claim 40, wherein the restriction endonuclease sites contained in the primer and the linker are not identical.

43. The method according to claim 36, further comprising removing the amplified vectors from the amplification cell type and retransfecting the vectors into an expression cell type.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 314 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: join(1..45, 49..306, 310..312)

( x i ) SEQUENCE DESCRIPTION: SEQ ID NO:1:

```
CCC TGC AGA TCG ATG AGC TCG CTA GCC AGC TGC CAG TGT GAT GGC         45
Pro Cys Arg Ser Met Ser Ser Leu Ala Ser Cys Gln Cys Asp Gly
  1             5                   10                  15

TGA CTT CTA GAG AAT TCC AGC ACA CTG GGC GGC CGC GAG CAG AAA CTG     93
    Leu Leu Glu Asn Ser Ser Thr Leu Gly Gly Arg Glu Gln Lys Leu
                    20                  25                  30

ATC TCT GAA GAA GAC CTG AAC TAC CCA TAC GAC GTC CCA GAC TAC GCT    141
Ile Ser Glu Glu Asp Leu Asn Tyr Pro Tyr Asp Val Pro Asp Tyr Ala
                35                  40                  45

TAC CCA TAC GAC GTC CCA GAC TAC GCT TAC CCA TAC GAC GTC CCA GAC    189
Tyr Pro Tyr Asp Val Pro Asp Tyr Ala Tyr Pro Tyr Asp Val Pro Asp
            50                  55                  60

TAC GCT CCA AAT AAA GGA AGT GGA ACC ACT TCA GGT ACT ACC CGT CTT    237
Tyr Ala Pro Asn Lys Gly Ser Gly Thr Thr Ser Gly Thr Thr Arg Leu
        65                  70                  75

CTA TCT GGG CAC ACG TGT TTC ACG TTG ACA GGT TTG CTT GGG ACG CTA    285
Leu Ser Gly His Thr Cys Phe Thr Leu Thr Gly Leu Leu Gly Thr Leu
    80                  85                  90

GTA ACC ATG GGC TTG CTG ACT TAG GTA CC                             314
Val Thr Met Gly Leu Leu Thr     Val
 95                 100
```

( 2 ) INFORMATION FOR SEQ ID NO:2:

( i ) SEQUENCE CHARACTERISTICS:
( A ) LENGTH: 102 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Pro Cys Arg Ser Met Ser Ser Leu Ala Ser Cys Gln Cys Asp Gly Leu
1               5                   10                  15

Leu Glu Asn Ser Ser Thr Leu Gly Gly Arg Glu Gln Lys Leu Ile Ser
            20                  25                  30

Glu Glu Asp Leu Asn Tyr Pro Tyr Asp Val Pro Asp Tyr Ala Tyr Pro
        35                  40                  45

Tyr Asp Val Pro Asp Tyr Ala Tyr Pro Tyr Asp Val Pro Asp Tyr Ala
    50                  55                  60

Pro Asn Lys Gly Ser Gly Thr Thr Ser Gly Thr Thr Arg Leu Leu Ser
65                  70                  75                  80

Gly His Thr Cys Phe Thr Leu Thr Gly Leu Leu Gly Thr Leu Val Thr
                85                  90                  95

Met Gly Leu Leu Thr Val
            100
```

( 2 ) INFORMATION FOR SEQ ID NO:3:

( i ) SEQUENCE CHARACTERISTICS:
( A ) LENGTH: 314 base pairs
( B ) TYPE: nucleic acid
( C ) STRANDEDNESS: single
( D ) TOPOLOGY: linear ( x i ) SEQUENCE DESCRIPTION: SEQ ID NO:3:

```
CCCTGCAGAT CGATGAGCTC GCTAGCCAGC TGCCAGTGTG ATGGCTGACT TCTAGAGAAT   60

TCCAGCACAC TGGGCGGCCG CGAGCAGAAA CTGATCTCTG AAGAAGACCT GAACTACCCA  120

TACGACGTCC CAGACTACGC TTACCCATAC GACGTCCCAG ACTACGCTTA CCCATACGAC  180

GTCCCAGACT ACGCTCCAAA TAAAGGAAGT GGAACCACTT CAGGTACTAC CCGTCTTCTA  240

TCTGGGCACA CGTGTTTCAC GTTGACAGGT TTGCTTGGGA CGCTAGTAAC CATGGGCTTG  300

CTGACTTAGG TACC                                                     314
```

( 2 ) INFORMATION FOR SEQ ID NO:4:

( i ) SEQUENCE CHARACTERISTICS:
( A ) LENGTH: 314 base pairs
( B ) TYPE: nucleic acid
( C ) STRANDEDNESS: single
( D ) TOPOLOGY: linear ( x i ) SEQUENCE DESCRIPTION: SEQ ID NO:4:

```
CCCTGCAGAT CGATGAGCTC GCTAGCCAGC TGCCAGTGTG ATGGCTGACT TCTAGAGAAT   60

TCCAGCACAC TGGGCGGCCG CGAGCAGAAA CTGATCTCTG AAGAAGACCT GAACTACCCA  120

TACGACGTCC CAGACTACGC TTACCCATAC GACGTCCCAG ACTACGCTTA CCCATACGAC  180

GTCCCAGACT ACGCTCCAAA TAAAGGAAGT GGAACCACTT CAGGTACTAC CCGTCTTCTA  240

TCTGGGCACA CGTGTTTCAC GTTGACAGGT TTGCTTGGGA CGCTAGTAAC CATGGGCTTG  300

CTGACTTAGG TACC                                                     314
```

( 2 ) INFORMATION FOR SEQ ID NO:5:

( i ) SEQUENCE CHARACTERISTICS:

( A ) LENGTH: 989 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 57..872

( x i ) SEQUENCE DESCRIPTION: SEQ ID NO:5:

```
CTGCAGATCG ATGAGCTCGC TAACCAGCTG CCAGTGTGGT GGAATTCGTC CTGAAC          56

ATG AGC CTC CTC CTC TCC TTC TAC CTG CTG GGG TTG CTT GTC AGT AGC       104
Met Ser Leu Leu Leu Ser Phe Tyr Leu Leu Gly Leu Leu Val Ser Ser
  1               5                  10                  15

GGG CAA GCT CTT CTT CAA GTG ACA ATT TCA CTT AGC AAA GTA GAG CTT       152
Gly Gln Ala Leu Leu Gln Val Thr Ile Ser Leu Ser Lys Val Glu Leu
             20                  25                  30

AGT GTT GGA GAA TCT AAA TTC TTC ACA TGT ACA GCG ATT GGT GAA CCT       200
Ser Val Gly Glu Ser Lys Phe Phe Thr Cys Thr Ala Ile Gly Glu Pro
         35                  40                  45

GAA AGT ATA GAT TGG TAT AAT CCT CAA GGA GAG AAG ATA ATT TCA ACA       248
Glu Ser Ile Asp Trp Tyr Asn Pro Gln Gly Glu Lys Ile Ile Ser Thr
     50                  55                  60

CAG AGG GTA GTA GTG CAA AAG GAA GGT GTT AGG TCA CGG TTA ACC ATC       296
Gln Arg Val Val Val Gln Lys Glu Gly Val Arg Ser Arg Leu Thr Ile
 65                  70                  75                  80

TAC AAT GCA AAT ATA GAA GAT GCA GGG ATA TAT CGT TGT CAA GCA ACA       344
Tyr Asn Ala Asn Ile Glu Asp Ala Gly Ile Tyr Arg Cys Gln Ala Thr
                 85                  90                  95

GAT GCC AAA GGA CAA ACA CAA GAA GCT ACA GTA GTT TTG GAA ATT TAC       392
Asp Ala Lys Gly Gln Thr Gln Glu Ala Thr Val Val Leu Glu Ile Tyr
            100                 105                 110

CAA AAA CTC ACT TTC AGA GAA GTG GTA TCT CCA CAA GAA TTC AAA CAA       440
Gln Lys Leu Thr Phe Arg Glu Val Val Ser Pro Gln Glu Phe Lys Gln
        115                 120                 125

GGA GAA GAT GCA GAA GTG GTT TGC CGA GTT AGC AGT TCA CCT GCA CCT       488
Gly Glu Asp Ala Glu Val Val Cys Arg Val Ser Ser Ser Pro Ala Pro
    130                 135                 140

GCT GTC AGC TGG TTG TAT CAT AAT GAG GAA GTC ACC ACT ATT TCC GAC       536
Ala Val Ser Trp Leu Tyr His Asn Glu Glu Val Thr Thr Ile Ser Asp
145                 150                 155                 160

AAT CGG TTC GCT ATG TTA GCA AAC AAT AAC CTG CAG ATT CTC AAC ATC       584
Asn Arg Phe Ala Met Leu Ala Asn Asn Asn Leu Gln Ile Leu Asn Ile
                165                 170                 175

AAT AAA AGT GAT GAA GGT ATA TAC AGA TGT GAA GGA AGA GTG GAG GCC       632
Asn Lys Ser Asp Glu Gly Ile Tyr Arg Cys Glu Gly Arg Val Glu Ala
            180                 185                 190

AGG GTA GGC GGC CGC GAG CAG AAA CTG ATT TCT GAA GAA GAC CTG AAC       680
Arg Val Gly Gly Arg Glu Gln Lys Leu Ile Ser Glu Glu Asp Leu Asn
        195                 200                 205

TAT CCA TAC GAC GTC CCA GAC TAC GCT TAC CCA TAC GAC GTC CCA GAC       728
Tyr Pro Tyr Asp Val Pro Asp Tyr Ala Tyr Pro Tyr Asp Val Pro Asp
    210                 215                 220

TAC GCT TAC CCA TAC GAC GTC CCA GAC TAC GCT CCA AAT AAA GGA AGT       776
Tyr Ala Tyr Pro Tyr Asp Val Pro Asp Tyr Ala Pro Asn Lys Gly Ser
225                 230                 235                 240

GGA ACC ACT TCA GGT ACT ACC CGT CTT CTA TCT GGG CAC ACG TGT TTC       824
Gly Thr Thr Ser Gly Thr Thr Arg Leu Leu Ser Gly His Thr Cys Phe
                245                 250                 255

ACG TTG ACA GGT TTG CTT GGG ACG CTA GTA ACC ATG GGC TTG CTA ACT       872
Thr Leu Thr Gly Leu Leu Gly Thr Leu Val Thr Met Gly Leu Leu Thr
            260                 265                 270
```

TAGGTACCTT CTGAGGCGGA AAGAACCAGC CGGATCCCTC GAGGGATCCA GACATGATAA 932

GATACATTGA TGAGTTTGGA CAAACCACAC TAGAATGCAG TGAAAAAAAT GCTTTAT 989

( 2 ) INFORMATION FOR SEQ ID NO:6:

( i ) SEQUENCE CHARACTERISTICS:
( A ) LENGTH: 272 amino acids
( B ) TYPE: amino acid
( D ) TOPOLOGY: linear ( i i ) MOLECULE TYPE: protein ( x i ) SEQUENCE DESCRIPTION: SEQ ID NO:6:

Met Ser Leu Leu Leu Ser Phe Tyr Leu Leu Gly Leu Leu Val Ser Ser
1 5 10 15

Gly Gln Ala Leu Leu Gln Val Thr Ile Ser Leu Ser Lys Val Glu Leu
20 25 30

Ser Val Gly Glu Ser Lys Phe Phe Thr Cys Thr Ala Ile Gly Glu Pro
35 40 45

Glu Ser Ile Asp Trp Tyr Asn Pro Gln Gly Glu Lys Ile Ile Ser Thr
50 55 60

Gln Arg Val Val Val Gln Lys Glu Gly Val Arg Ser Arg Leu Thr Ile
65 70 75 80

Tyr Asn Ala Asn Ile Glu Asp Ala Gly Ile Tyr Arg Cys Gln Ala Thr
85 90 95

Asp Ala Lys Gly Gln Thr Gln Glu Ala Thr Val Val Leu Glu Ile Tyr
100 105 110

Gln Lys Leu Thr Phe Arg Glu Val Val Ser Pro Gln Glu Phe Lys Gln
115 120 125

Gly Glu Asp Ala Glu Val Val Cys Arg Val Ser Ser Ser Pro Ala Pro
130 135 140

Ala Val Ser Trp Leu Tyr His Asn Glu Glu Val Thr Thr Ile Ser Asp
145 150 155 160

Asn Arg Phe Ala Met Leu Ala Asn Asn Asn Leu Gln Ile Leu Asn Ile
165 170 175

Asn Lys Ser Asp Glu Gly Ile Tyr Arg Cys Glu Gly Arg Val Glu Ala
180 185 190

Arg Val Gly Gly Arg Glu Gln Lys Leu Ile Ser Glu Glu Asp Leu Asn
195 200 205

Tyr Pro Tyr Asp Val Pro Asp Tyr Ala Tyr Pro Tyr Asp Val Pro Asp
210 215 220

Tyr Ala Tyr Pro Tyr Asp Val Pro Asp Tyr Ala Pro Asn Lys Gly Ser
225 230 235 240

Gly Thr Thr Ser Gly Thr Thr Arg Leu Leu Ser Gly His Thr Cys Phe
245 250 255

Thr Leu Thr Gly Leu Leu Gly Thr Leu Val Thr Met Gly Leu Leu Thr
260 265 270

( 2 ) INFORMATION FOR SEQ ID NO:7:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:7:

CTCGCTAGCC AATGCCGGCG TTGGCGCGCG ACGGC 35

( 2 ) INFORMATION FOR SEQ ID NO:8:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:8:

CTCGCGGCCG CGTTGTCTTG GATGAAAGGG AAG 33

( 2 ) INFORMATION FOR SEQ ID NO:9:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:9:

CTGTACGGAA GTGTTACTTC TGCTC 25

( 2 ) INFORMATION FOR SEQ ID NO:10:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:10:

CTCGCGGCCG CTGGCTGCAA CAGGAGGTAA CATAAATG 38

( 2 ) INFORMATION FOR SEQ ID NO:11:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:11:

CTTCTGCAGG GTTCCCAG 18

( 2 ) INFORMATION FOR SEQ ID NO:12:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:12:

CTCGCGGCCG CTCCGTCCAT CTTCATCCAG 30